United States Patent
Kandelman et al.

(10) Patent No.: US 6,669,475 B2
(45) Date of Patent: Dec. 30, 2003

(54) PERSONAL INTERPROXIMAL DENTAL SURFACE CLEANING AND DRUG DELIVERY DEVICE

(76) Inventors: Stanislas Kandelman, 44 rue Servan, Paris 75011 (FR); Daniel Kandelman, 7380 Maynard, Montréal, Québec (CA), H3R 3B4

( * ) Notice: Subject to any disclaimer, the term of this patent is extended or adjusted under 35 U.S.C. 154(b) by 0 days.

(21) Appl. No.: 10/158,942

(22) Filed: Jun. 3, 2002

(65) Prior Publication Data

US 2003/0224320 A1 Dec. 4, 2003

(51) Int. Cl.$^7$ .................................. A61C 5/04
(52) U.S. Cl. ..................... 433/89; 433/80; 601/139; 132/322
(58) Field of Search .............. 433/80, 82, 89; 601/139, 141, 162; 132/321, 322, 329; 15/167.1

(56) References Cited

U.S. PATENT DOCUMENTS

| | | |
|---|---|---|
| 2,008,206 A | 7/1935 | Grant |
| 2,793,381 A | 5/1957 | McWhorter |
| 3,391,696 A | 7/1968 | Woodward |
| 3,480,009 A | 11/1969 | Sinai |
| 3,547,110 A * | 12/1970 | Balamuth |
| 3,636,947 A * | 1/1972 | Balamuth |
| 3,910,706 A | 10/1975 | Del Bon |
| 4,049,354 A | 9/1977 | O'Rourke |
| 4,411,623 A * | 10/1983 | Axelsson ................... 433/80 |
| 4,457,711 A | 7/1984 | Maloney et al. |
| 4,640,637 A | 2/1987 | Witnthrop |
| 4,691,404 A | 9/1987 | Tarrson et al. |
| 4,805,646 A * | 2/1989 | Shimenkov ................ 132/329 |
| 4,828,420 A * | 5/1989 | Otsuka et al. ............. 401/268 |
| 4,846,200 A | 7/1989 | Wiley |
| 4,863,380 A | 9/1989 | Creed |
| 4,958,751 A * | 9/1990 | Curtis et al. ............... 433/80 |
| 5,098,291 A * | 3/1992 | Curtis et al. ............... 433/89 |
| 5,098,297 A | 3/1992 | Chari et al. |
| 5,125,834 A * | 6/1992 | Swan ........................ 433/80 |
| 5,152,742 A | 10/1992 | Simpson |
| 5,283,924 A | 2/1994 | Kaminski et al. |
| 5,507,646 A | 4/1996 | Roth |
| 5,558,518 A * | 9/1996 | Bab et al. ................. 433/80 |
| 5,609,170 A | 3/1997 | Roth |
| 5,775,346 A * | 7/1998 | Szyszkowski .............. 132/329 |
| 5,829,976 A | 11/1998 | Green |
| 6,082,999 A * | 7/2000 | Tcherny et al. ............ 433/80 |
| 6,418,940 B1 * | 7/2002 | Tcherny et al. ............ 132/321 |

\* cited by examiner

*Primary Examiner*—Ralph A. Lewis
(74) *Attorney, Agent, or Firm*—Robic

(57) ABSTRACT

Disclosed is a device for use to clean interproximal dental surfaces, subgingival areas and periodontal pockets and deliver a drug to these surfaces, areas and pockets after they have been cleaned. The device has a reservoir for storing and supplying the drug. The reservoir acts as a handle and has an outlet at one extremity. The device also has a needle with an internal channel through which the drug may flow. The needle is made of three successive sections including a clipping section, a cleaning section and an applicator section. The clipping section is connected to the outlet of the reservoir in such a manner as to place the channel of the needle in open communication with the reservoir. The cleaning section has an outer scrubbing surface that is sized to be inserted between teeth in order to clean the interproximal dental surfaces, subgingival areas and periodontal pockets. The applicator section projects away from the cleaning segment in a direction opposite to the clipping section. It has a plurality of perforations that allows the drug supplied from the reservoir through the channel, to be delivered to the interproximal dental surfaces, subgingival areas and periodontal pockets after their cleaning has been completed. Inasmuch as the applicator section is separate from the cleaning section and located in a position opposite to the handle, the drug may be delivered onto the areas, surfaces or pockets that have been cleanedwhile reducing the risk for this drug to be withdrawn by the scrubbing surface of the cleaning section when the same is removed from between the teeth.

18 Claims, 3 Drawing Sheets

PERSONAL INTERPROXIMAL DENTAL SURFACE CLEANING AND DRUG DELIVERY DEVICE

FIELD OF INVENTION

The present invention relates to an interproximal dental surface cleaning and drug delivery device that is designed to clean the interproximal dental surfaces, subgingival areas and periodontal pockets of his or her user, and subsequently allow delivery of a drug onto the same surfaces, areas and pockets to treat dental pathological problems. Such pathological problems include but are not limited to hypersensitivity, initial dental caries and periodontal inflammations.

BACKGROUND OF THE INVENTION

It is known that the interproximal dental surfaces of the teeth are hard to clean because it is difficult to reach these surfaces with conventional and/or electric toothbrushes. The bristles of these brushes cannot penetrate easily from the buccal or lingual faces of the teeth under the interproximal teeth contact points, and consequently these points cannot be cleaned adequately.

When there is an adequate contact between the interproximal dental surfaces and the anatomic configuration of the subgingival area is healthy (i.e. when there is no bone retraction nor periodontal pockets), use can be made of devices like dental flosses, hydrotherapeutic instruments, interdental stimulators or tooth picks, to clean the interproximal surfaces.

However, in the presence of periodontal pockets or gum retraction, the subgingival areas cannot be properly cleaned by the above mentioned devices since they cannot penetrate in the depth of the periodontal pockets due either to a lack of rigidity (in the case of dental floss) or to difficulties encountered for reaching the depths of a periodontal pocket or reaching the bottom of the tooth surface under the marginal crests of the gingival.

The most efficient devices presently used to overcome the above situations are interproximal brushes and toothpicks, like the one disclosed in U.S. Pat. No. 4,691,404 (Tarrson et al) issued on Sep. 8, 1987.

These devices are actually recommended for adults with large interproximal areas which can easily retain food debris and dental plaque, for those presenting gingival inflammation, and for those exhibiting early stages of periodontal diseases. They are also recommended for maintenance after periodontal surgery.

However, since it is difficult to clean adequately the tooth surfaces and areas with the above mentioned devices and since dental plaque in the presence of food debris and bacteria are known to adhere on the tooth surfaces in less than 24 hours, interproximal pathologies are frequently observed, which include dental caries, and root caries and hypersensitivity.

Dental caries are often initiated on interproximal dental surfaces since it is difficult to maintain adequate oral hygiene on these areas. The initial steps of caries correspond histopathologically to sites of demineralization which, without treatment (i.e. topical fluoride for instance), may progress to cavitation. This initial step is reversible but require restorative treatment.

Root caries occur when there is gum recession as a result of a prolonged gingival and/or malocclusion disorder such as premature teeth contacts. In such a case, the junction in between enamel and cementum is not anymore protected by the gingival crest and the exposed cementum which is more porous than enamel, can very easily develop root caries.

Hypersensitivity is another unpleasant pathology associated with dentinal and cementum hypersensitivity which may be observed after periodontal surgery. In such a case, the tooth surfaces are often suddenly exposed since they are no longer protected by a muco-gingival layer. Thus, they become very sensitive to thermic or tactile stimuli.

To tentatively overcome the above mentioned drawbacks, devices have been developed to treat dental pathologies which occur in interproximal tooth surfaces, sub-gingival areas and periodontal pockets. Typiclally, these devices for treating dental pathologies comprise a handle to which is connected a cleaning instrument provided with a scrub material. The handle is devised to act as a reservoir for a drug that can be delivered to the cleaned surfaces, areas and pockets.

U.S. Pat. No. 4,863,380 (Creed) issued on Sep. $5^{th}$, 1989 is illustrative of such devices. It discloses a device comprising a tubular neck that leads up from a reservoir to a rubber tip. The rubber tip has holes in its sidewall for discharging a drug between the teeth into the pockets and around the gums. The drug is expelled from the reservoir by squeezing the same. To prevent fluid in the mouth from re-entering the neck when squeezing pressure is removed, a check valve is used.

U.S. Pat. No. 5,283,924 (Kaminski et al.) issued Feb. $4^{th}$, 1994 discloses a dental instrument including a boss coated with a resilient open-cell polymeric foam for use in oral hygiene. This patent discloses that the foam can be impregnated with a drug in the form of a coating, solution, pasteior gel for treating germs or teeth.

U.S. Pat. No. 5,829,976 (Green) issued Feb. $8^{th}$, 1998 discloses a disposable fibrous dental applicator tip that is fed with a drug via a cannula. The applicator tip is specifically designed to massage the interproximal root surfaces and simultaneously deliver the drug to sources of periodontal diseases.

All of these known devices are interesting. However, they are devised to deliver the drug to the pathological sites via their cleaning sections, viz. their rubber tip, foam covered boss or applicator tip. As a result there is a permanent risk of having the drug applied to the interproximal dental surfaces, subgingival areas and periodontal pockets removed from the same when the tip or boss, are removed from between the teeth.

SUMMARY OF THE INVENTION

It is an object of the present invention to provide an interproximal dental surface cleaning and drug delivery device which can be used for cleaning and delivery of drug to the interproximal tooth surfaces, sub-gingival areas, and periodontal pockets without risk of withdrawal of the drug by the cleaning section of said device when the same is removed.

More specifically, the object of the present invention is to provide an interproximal dental surface cleaning and drug delivery device comprising:

a reservoir for storing and supplying a drug to treat pathological problems on interproximal dental surfaces, subgingival areas and periodontal pockets, the reservoir acting as a handle and comprising an outlet at one extremity; and a needle comprising an internal channel through which the medicament may flow.

In accordance with the invention, the needle comprises:

a clipping section connected to the outlet of the reservoir in such a manner as to place the channel of the needle in open communication with the reservoir;

a cleaning section having an outer scrubbing surface sized to be inserted between teeth in order to clean interproximal dental surfaces, subgingival areas and periodontal pockets, said cleaning section having no perforation opening into the internal channel; and an applicator section projecting from the cleaning segment opposite to the clipping section, the applicator section having a relatively smooth outer surface and comprising of a plurality of perforations allowing the drug supplied from the reservoir through the channel to be delivered to the interproximal dental surfaces, subgingival areas and periodontal pockets after their cleaning has been completed.

The invention essentially lies in that the applicator section is "separate" from the cleaning section and located in a position opposite to the handle. Thus, the user may deliver the drug stored in the handle onto the areas, surfaces or pockets that have been cleaned while reducing the risk for the drug to be withdrawn by the scrubbing surface of the cleaning section when the same is removed from between the teeth. In other words, the device according to the invention allows the drug to be delivered after cleaning of the subgingival areas, interproximal dental surfaces and/or peridontal pockets to be treated while allowing the drug to be left on place for a prolonged period of time.

As aforesaid, the device according to the invention is particularly convenient for delivery of drugs on specific sites like tooth surfaces with demineralized spots or initial caries, zones of hypersensitivity, sub-gingival areas with inflammation and deep periodontal pockets. Such may be very useful for adult persons with gum recession, early periodontal diseases, large interproximal spaces or after periodontal surgery.

The invention will be better understood upon reading the following non-restrictive description of several preferred embodiments thereof, made with reference to the accompanying drawings.

DETAILED DESCRIPTION OF SEVERAL PREFERRED EMBODIMENTS OF THE INVENTION

Figure 1:
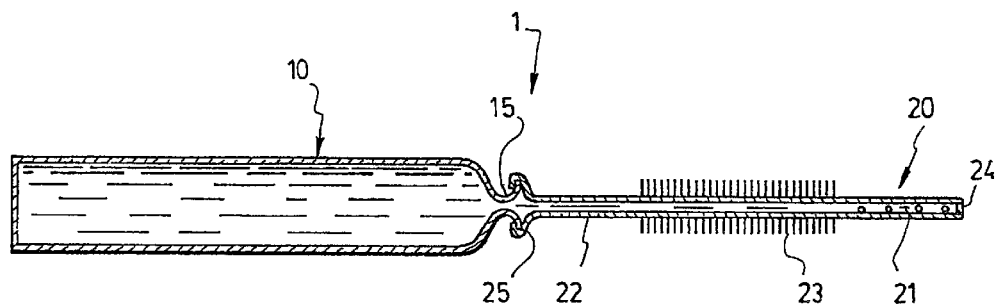
FIG. 1 is a cross-sectional side view of an interproximal dental surface cleaning and drug delivery device according to a first preferred embodiment of the invention, where the cleaning section and applicator section are in line with the reservoir.

In the following description, the same numerical references refer to the same or similar structural elements.

Whatever be the illustrated preferred embodiments, the interproximal dental surface cleaning and drug delivery device (1) according to the invention comprises a reservoir (10) for storing and supplying a drug to treat pathological problems on interproximal dental surfaces, subgingival areas and periodontal pockets.

It also comprises a needle (20) having an internal channel (21) through which the drug may flow. The needle comprises three successive sections including a clipping section (22), a cleaning section (23) and an applicator section (24).

The reservoir (10) is devised to act as a handle. It comprises an outlet (15) at one extremity, to which the clipping section (22) is connected in such a manner as to place the channel (21) of the needle (20) in open communication with the reservoir (10) to allow the drug to flow through it.

The Reservoir

As aforesaid, the reservoir (10) is used for storing and supplying the drug. It is also intended to be used as a handle.

It may consist of a tube made of thermoplastic material, that may be 3.5 to 5.5 cm long and 0.5 to 0.8 cm wide. Preferably, its size is selected so as to allow delivery of the drug stored in it for the cleaning and treatment of the interproximal areas of at least one complete dentist adult month (30 to 32 applications).

Figure 2:
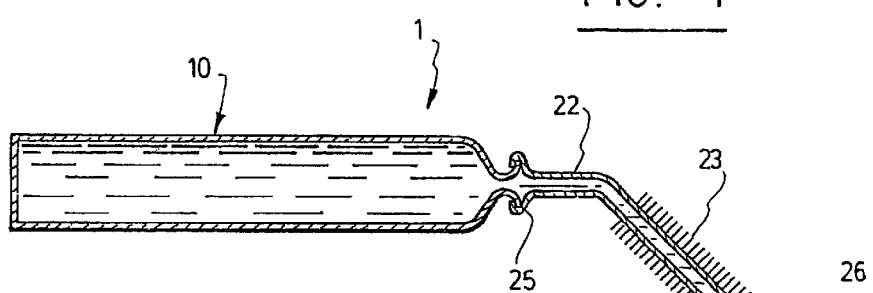
FIG. 2 is a view similar to FIG. 1, showing the same device with the cleaning section and applicator section in inclined position.

In the first preferred embodiment of the invention shown in FIGS. 1 and 2, the reservoir (10) is made of a semi-solid deformable material that is sufficiently rigid to make the reservoir useful as a handle, but soft enough to allow delivery of the drug to the needle (20) by pinching.

Figure 3:
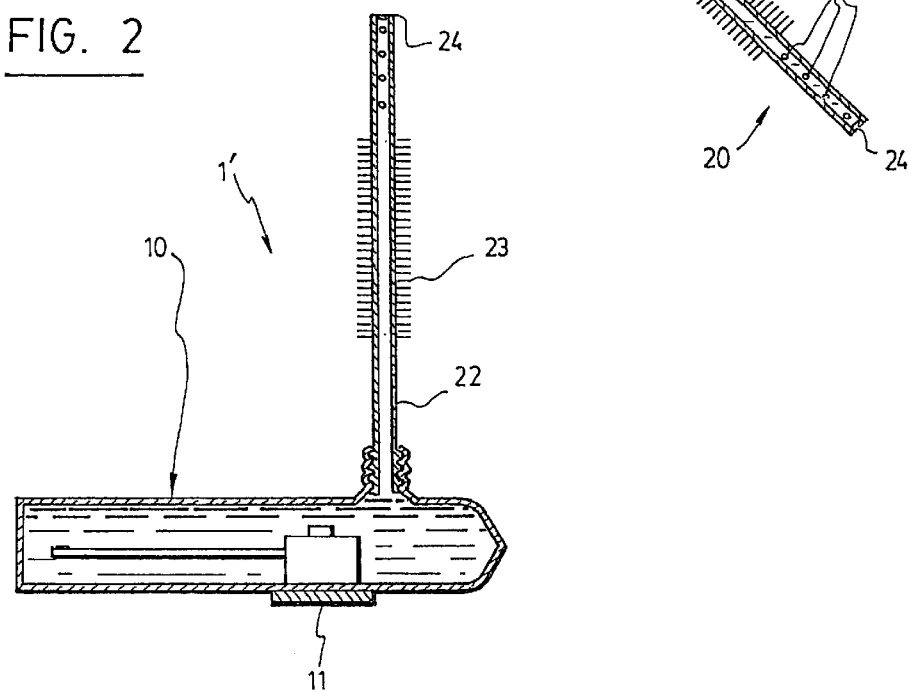
FIG. 3 is a side view of an interproximal dental surface cleaning and drug delivery device according to a second preferred embodiment of the invention, where the reservoir is provided with a finger-actuatable pump to deliver the drug to the needle.
Figure 4:
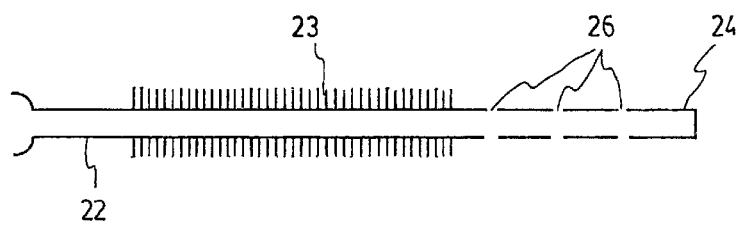
FIGS. 4 to 9 are side views of needles of different structures that can be used in the device according to the invention.

In the second preferred embodiment shown in FIG. 3, the reservoir (10) is made of a rigid material and comprises a finger-actuatable pump, (11) for "pushing" the drug out of the reservoir and delivery it to the needle.

Preferably, the reservoir is in the form of a disposable cartridge. However, it could also be devised to be refilled by suitable means for further use.

The outlet (15) located at the extremity of the reservoir (10) is preferably shaped as a neck having a diameter of about 0.5 mm, on which connector (25) provided at the free end of the clipping section (22) of the needle (20) can be snapped or screwed. Such allows the needle (10) to be replaced whenever desired. The neck of the reservoir (10) can be located axially on top of the reservoir (10) as shown in FIG. 1 or 2, or laterally close to the top edge of the reservoir as shown in FIG. 3, depending on the user's requirement or need.

Of course, the volume of the reservoir must be sufficient to store enough drug for delivery to all the inter dental spaces and sub-gingival areas of the mouth.

During the manufacture of the device (1), the reservoir (10) is preferably sealed after it has been filled up with the drug. Such a sealing may be achieved with a cap having a size adjusted to the size of the neck in order to allow perfect bonding and maintain into the reservoir the drug that is usually in liquid, varnish or gel form. The top of the cap may be provided with rigid tip to facilitate perforation of a sealing membrane that may also be applied to the opening of the neck prior to installing the cap.

As may be appreciated, the material that is selected to manufacture the reservoir (10) must fulfil the three following characteristics:

rigidity;

flexibility; and chemical stability with regard to the drug which is in the reservoir.

The Needle

As aforesaid, the needle (20) comprises three successive sections which, altogether, may have a length of 2 to 2.5 cm.

The first one of these sections, called "clipping section (20)", has its free end provided with the connector (25) mentioned, hereinabove, thereby making it connectable in a detachable manner to the outlet (25) of the reservoir (10). Such a "detachability" makes the needle interchangeable and such is interesting inasmuch as, in practice, it may be convenient to change the needle after a given period of time, like one month application. The detachable connection can be achieved by snapping or by screwing depending on the structure of the neck (15) of the reservoir (10) and the one of the corresponding connector of the clipping section (22).

As shown in FIG. 2, the clipping section (22) is preferably made of a semi-rigid deformable material. Such a material permits to bend the clipping section (22) and thus to adjust the relative position of the adjacent cleaning section (23) and applicator section (24) with respect to the reservoir (10).

In practice, the channel (21) extending through the clipping section (22) and the subsequent sections of the needle has a diameter of 0.2 to 0.5 mm. Such is sufficient to allow proper delivery of the drug from the reservoir along all of the needle.

The second section, called "cleaning section (23)", extends from the clipping section (22) in a direction opposite to the reservoir (10) and is provided with an outer scrubbing surface (30).

To be efficient, such a cleaning section (23) must be of a sufficient length, diameter and strength to allow its insertion between the teeth in order to clean the interproximal dental surfaces, subgingival areas and periodontal pockets. By way of example, it can be from 1 to 1.5 cm long.

The scrubbing surface (30) may comprise tufted scrub material consisting of fine bristles as shown in FIGS. 1 to 4. These bristles may be casted from the same plastic material as the remaining of the needle or they may be made of a different material. In the latter case, they can be inserted into the body of the cleaning section either manually or mechanically with a Carlson® model machine.

Preferably, the cleaning section is thus made of polypropylene, ABS or TPX and the bristles are made of Nylon 6.12 and have a length of 1.5 mm and a diameter of 180 µm.

Figure 5:
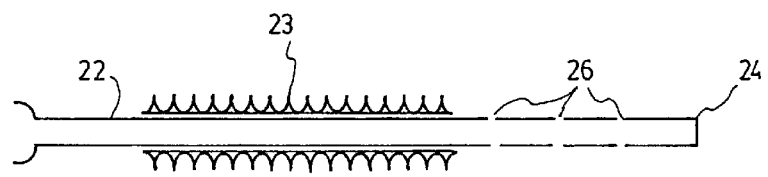
Figure 6:
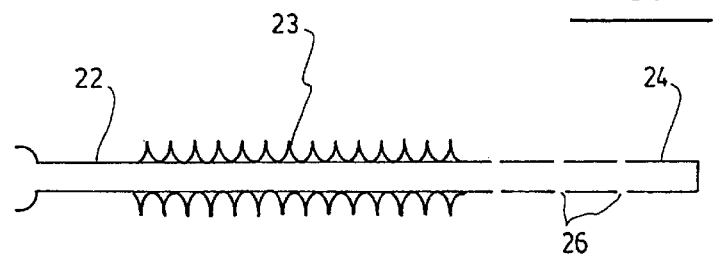
Figure 7:
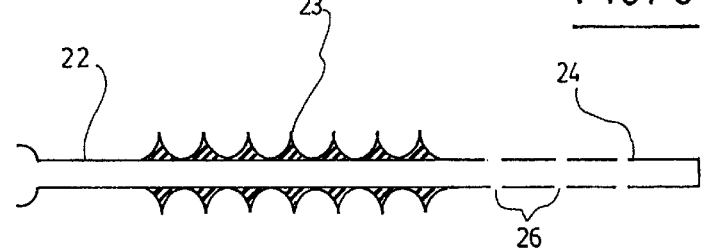
Figure 9:
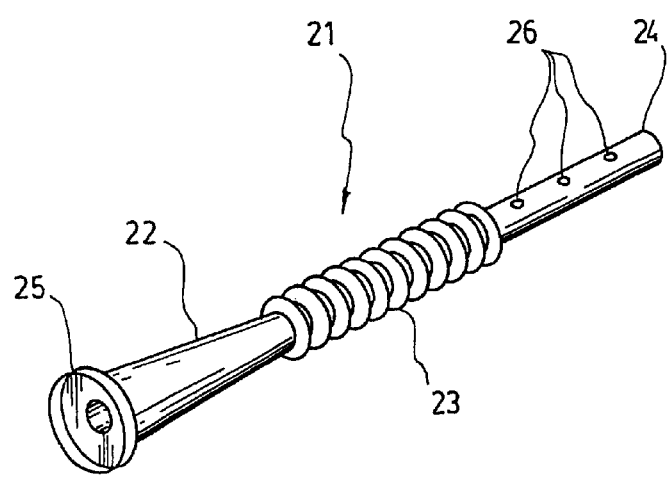

Alternatively, the scrubbing surface (30) may consist of adjacent ring-shaped corrugations (see FIG. 9) or of a plurality cone-shaped corrugations projecting radially externally (see FIGS. 5 to 7). All of these corrugations can be made from the same plastic material as the needle (see FIGS. 4, 6 and 9) or of a different material (see FIGS. 5 and 7).

Preferably, the corrugations are spaced apart so that there is about 1 mm between each other and about its corrugations over the length of the cleaning section.

Figure 8:
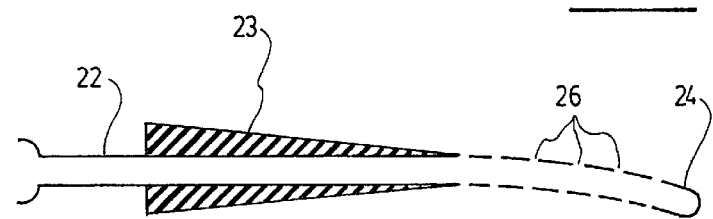

The scrubbing surface (30) may also consist of a cone made of thermoplastic elastomer as shown in FIG. 8, which tapers from the clipping section toward the applicator section over a length of 1 to 1.5 cm.

The third section, called "applicator section (24)", projects from the cleaning section (23) in a direction opposite to the clipping section (22). It has a plurality of perforations (26) which allows the drug supplied from the reservoir (10) and through the channel (24) to be delivered onto the interproximal dental surfaces, subgingival areas and periodontal pockets after their cleaning has been completed.

The applicator section may be straight or slightly bent as shown in FIG. 8. It preferably comprises 6 to 8 perforations (26) having a diameter of 0.5 to 1 mm in order to allow the drug to be delivered whatever be its consistence, viz. as a liquid, a gel or a varnish or a cream.

As aforesaid, the needle (21) can be made of one piece casted within a mold, as shown in FIGS. 4, 6, 7 and 9. In such a case, the plastic material is preferably PVC, TPE or Santoprene® rubber.

Alternatively, as shown in FIGS. 5 and 8, its main body including the clipping section, the body of the cleaning section and the applicator section, can be made of one casted piece of, for example, PP, ABS or TPX, and the scrubbing surface with a different material such as, for example, bristles made of PP, ABS, TPS or Santoprene®.

As it can be appreciated, the interproximal dental surface cleaning and drug delivery device (1) disclosed hereinabove is interesting as compared to the existing devices, in that it allows delivery of a drug via the applicator section (24) of the needle, to the interproximal dental surfaces, subgingival areas and periodontal pockets after removal of the cleaning section (23) of the needle.

For this purpose, the device (1) is preferably used as follows:

in a first step, the interpromixal dental surfaces, the sub-gingival areas and periodontal pockets are cleaned by means of a brushing carried out with the cleaning section of the needle after insertion of the same between the teeth and in a second subsequent step, the drug is delivered through the applicator section after the cleaning section has been removed from between the teeth, thereby avoiding the risk to withdraw the drug with the scrubbing surface of the device.

Of course, numerous modifications could be made to the above-described embodiments without departing from the scope of the invention as defined in the appended claims.

What is claimed is:

1. An interproximal dental surface cleaning and drug delivery device comprising:
    a reservoir for storing and supplying a drug to treat pathological problems on interproximal dental surfaces, subgingival areas and periodontal pockets, said reservoir acting as a handle and comprising an outlet at one extremity; and
    a needle comprising an internal channel through which the drug may flow, said needle comprising:
        a clipping section connected to the outlet of the reservoir in such a manner as to place the channel of the needle in open communication with the reservoir;
        a cleaning section having an outer scrubbing surface sized to be inserted between teeth in order to clean interproximal dental surfaces, subgingival areas and periodontal pocket, said cleaning section having no perforation opening into the internal channel; and
        an applicator section projecting from the cleaning segment opposite to the clipping section, said applicator section having a relatively smooth outer surface and comprising of a plurality of perforations allowing the drug supplied from the reservoir through the channel to be delivered to said interproximal dental surfaces, subgingival areas and periodontal pockets after their cleaning has been completed.

2. A device as claimed in claim 1, wherein the reservoir is made of a semi-solid deformable material, whereby delivery of the drug to the needle is achieved by pinching the reservoir.

3. A device as claimed in claim 2, wherein clipping section is made of a semi-rigid deformable material to attain multiple positions and thus to adjust the relative position of the cleaning section and applicator section with respect to the reservoir.

4. A device as claimed in claim 3, wherein the scrubbing surface comprises tufted scrub material of sufficient length and strength to clean the interproximal dental surfaces, subgingival areas and periodontal pockets.

5. A device as claimed in claim 1, wherein the reservoir comprises a pump for delivering the drug to the needle.

6. A device as claimed in claim 5, wherein clipping section is made of a semi-rigid deformable material to attain multiple positions and thus to adjust the relative position of the cleaning section and applicator section with respect to the reservoir.

7. A device as claimed in claim 6, wherein the scrubbing surface comprises tufted scrub material of sufficient length and strength to clean the interproximal dental surfaces, subgingival areas and periodontal pockets.

8. A device as claimed in claim 1, wherein the reservoir is devised to be refilled when necessary.

9. A device as claimed in claim 1, wherein the reservoir is in the form of a disposable cartridge.

10. A device as claimed in claims 1, wherein the clipping section is devised to be snapped in a detachable manner to the outlet of the reservoir.

11. A device as claimed in claim 1, wherein the clipping section is devised to be screwed in a detachable manner to the outlet of the reservoir.

12. A device as claimed in claim 1, wherein the clipping section is made of a semi-rigid deformable material to attain multiple positions and thus to adjust the relative position of the cleaning section and applicator section with respect to the reservoir.

13. A device as claimed in claim 1, wherein the scrubbing surface comprises tufted scrub material of sufficient length and strength to clean the interproximal dental surfaces, subgingival areas and periodontal pockets.

14. A device as claimed in claim 13, wherein the tufted scrub material consists of bristles.

15. A device as claimed in claim 1, wherein the scrubbing surface consists of adjacent ring-shaped corrugations.

16. A device as claimed in claim 1, wherein the scrubbing surface consists of cone shaped corrugations projecting radially externally.

17. A device as claimed in claim 1, wherein the scrubbing surface tapers from the clipping section towards the applicator section.

18. A device as claimed in claim 1, wherein the applicator section comprises 6 to 8 perforations.

* * * * *